United States Patent
Choi et al.

(10) Patent No.: US 9,622,764 B2
(45) Date of Patent: Apr. 18, 2017

(54) SURGICAL INSTRUMENT

(75) Inventors: Hyun-Do Choi, Yongin-si (KR);
Yeon-ho Kim, Hwaseong-si (KR);
Jin-woo Cho, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1554 days.

(21) Appl. No.: 13/219,168

(22) Filed: Aug. 26, 2011

(65) Prior Publication Data

US 2012/0143174 A1    Jun. 7, 2012

(30) Foreign Application Priority Data

Dec. 3, 2010    (KR) ........................ 10-2010-0122947

(51) Int. Cl.
| | | |
|---|---|---|
| A61B 19/00 | (2006.01) | |
| A61B 17/29 | (2006.01) | |
| A61B 34/00 | (2016.01) | |
| A61B 34/30 | (2016.01) | |
| A61B 17/00 | (2006.01) | |

(52) U.S. Cl.
CPC .............. *A61B 17/29* (2013.01); *A61B 34/30* (2016.02); *A61B 34/70* (2016.02); *A61B 2017/00402* (2013.01); *A61B 2017/2902* (2013.01); *A61B 2017/2906* (2013.01); *A61B 2017/2908* (2013.01); *A61B 2017/2927* (2013.01)

(58) Field of Classification Search
CPC .............. A61B 19/22; A61B 2217/005; A61B 17/00234; A61B 17/0218; A61B 17/0469; A61B 17/12013; A61B 17/1285; A61B 17/320016; A61B 17/3207; A61B 19/20; A61B 19/52; A61B 19/201; A61B 19/203; A61B 19/5244; A61B 19/2242; A61F 9/00745
USPC ..................................... 606/1, 130
See application file for complete search history.

(56) References Cited

U.S. PATENT DOCUMENTS

| | | |
|---|---|---|
| 5,792,135 A | 8/1998 | Madhani et al. |
| 7,155,316 B2 | 12/2006 | Sutherland et al. |
| 9,020,640 B2* | 4/2015 | Yeung .................... A61B 19/20 |
| | | 604/177 |

(Continued)

FOREIGN PATENT DOCUMENTS

| | | |
|---|---|---|
| JP | 5-123325 A | 5/1993 |
| JP | 8-89509 A | 4/1996 |

(Continued)

OTHER PUBLICATIONS

Communication dated Jan. 4, 2017, issued by the Korean Intellectual Property Office in corresponding Korean Application No. 10-2010-0122947.

(Continued)

*Primary Examiner* — Ahmed Farah
(74) *Attorney, Agent, or Firm* — Sughrue Mion, PLLC

(57) ABSTRACT

A surgical instrument utilized in a minimally invasive surgery is provided. The surgical instrument includes an end effecter configured to conduct a surgical operation, a piezoelectric driver configured to generate motive power, a power transmitting unit configured to transmit the motive power generated by the piezoelectric driver to the end effecter to operate the end effecter, and a housing which encloses the power transmitting unit and the at least one piezoelectric driver.

15 Claims, 12 Drawing Sheets

(56) References Cited

U.S. PATENT DOCUMENTS

| | | | |
|---|---|---|---|
| 2004/0146433 A1* | 7/2004 | Massaro | B01L 3/022 |
| | | | 506/33 |
| 2005/0267406 A1* | 12/2005 | Hassler, Jr. | A61F 5/0003 |
| | | | 604/96.01 |
| 2011/0077504 A1* | 3/2011 | Fischer | A61B 34/30 |
| | | | 600/411 |
| 2013/0123759 A1* | 5/2013 | Kang | A61B 34/75 |
| | | | 606/1 |
| 2016/0045273 A1* | 2/2016 | Campbell | A61B 19/2203 |
| | | | 606/130 |

FOREIGN PATENT DOCUMENTS

| | | |
|---|---|---|
| JP | 2002-504863 A | 2/2002 |
| KR | 10-0585458 A | 6/2006 |
| KR | 10-0778387 B1 | 11/2007 |
| KR | 10-2010-0090528 A | 8/2010 |

OTHER PUBLICATIONS

Communication dated Feb. 1, 2017 issued by the Korean Intellectual Property Office in counterpart Korean Patent Application No. 10-2017-0010546.

* cited by examiner

SURGICAL INSTRUMENT

CROSS-REFERENCE TO RELATED APPLICATION(S)

This application claims the benefit under 35 U.S.C. §119(a) of Korean Patent Application No. 10-2010-0122947, filed on Dec. 3, 2010, in the Korean Intellectual Property Office, the entire disclosure of which is incorporated herein by reference for all purposes.

BACKGROUND

1. Field

The following description relates to surgical instrument utilized for minimally invasive surgery.

2. Description of the Related Art

Minimally invasive surgery (MIS) may be performed by inserting a surgical instrument into a number of small incisions in a body. Accordingly, an MIS may minimize the number of the surgical openings, and thus may reduce the amount of pain and scar from the surgery incision(s). Further, an MIS may cause relatively less change in metabolism of a patient after surgery, and thus may result in a shorter recovery period.

Hence, a patient who has undergone an MIS may have shorter hospital stay, and can be back to normal life after a short period of time.

A typical form of MIS is abdominal surgery with minimally invasive inspection and surgery of an abdomen. In the abdominal surgery, a surgical robot is utilized to diminish pain from the surgery and produce more successful surgical outcome.

The surgical robot may include a passive arm which is moved manually at a preparation stage before surgery, an active arm which moves actively according to a movement of an operator during surgical operation, and a surgical instrument which directly carries out the surgery procedures with wrists and forceps. Wires are used to transfer the movement and force of the surgical instrument, and a driver is provided to the active arm to control the wires.

SUMMARY

One or more embodiments provide a surgical instrument which may be advantageous in the reduction of size of a surgical robot and be easy to expand to a multi-joint configuration.

According to an aspect of an embodiment, there is provided a surgical instrument including: at least one end effecter configured to conduct a surgical operation; at least one piezoelectric driver configured to generate motive power; a power transmitting unit configured to transmit the motive power generated by the at least one piezoelectric driver to the at least one end effecter to operate the at least one end effecter; and a housing which encloses the power transmitting unit and the at least one piezoelectric driver.

BRIEF DESCRIPTION OF THE DRAWINGS

The above and other aspects will become more apparent by describing in detail embodiments with reference to the attached drawings in which.

DETAILED DESCRIPTION

Figure 1:
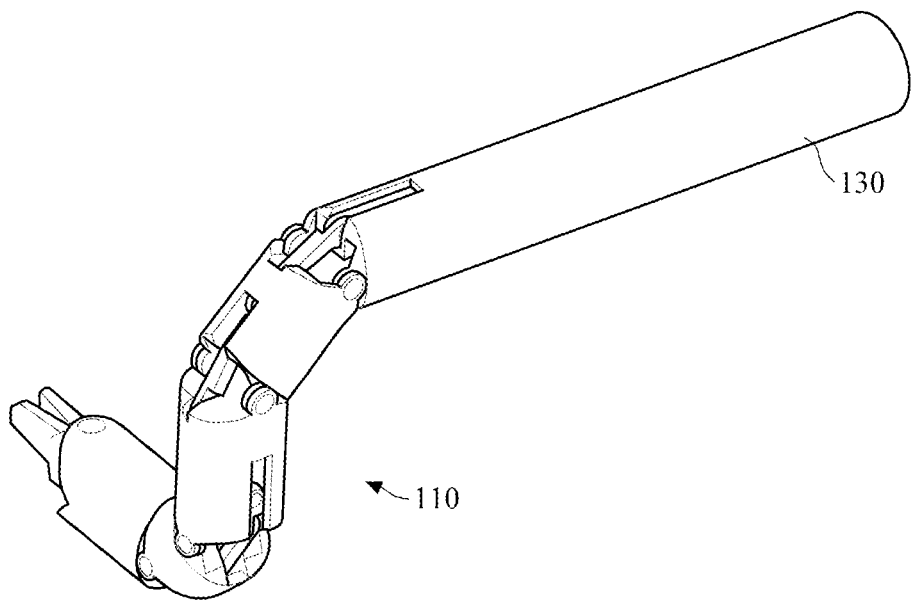
FIG. 1 is a diagram illustrating a perspective view of a surgical instrument according to an embodiment.

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Throughout the drawings and the detailed description, unless otherwise described, the same drawing reference numerals will be understood to refer to the same elements, features, and structures. The relative size and depiction of these elements may be exaggerated for clarity, illustration, and convenience.

Figure 2:
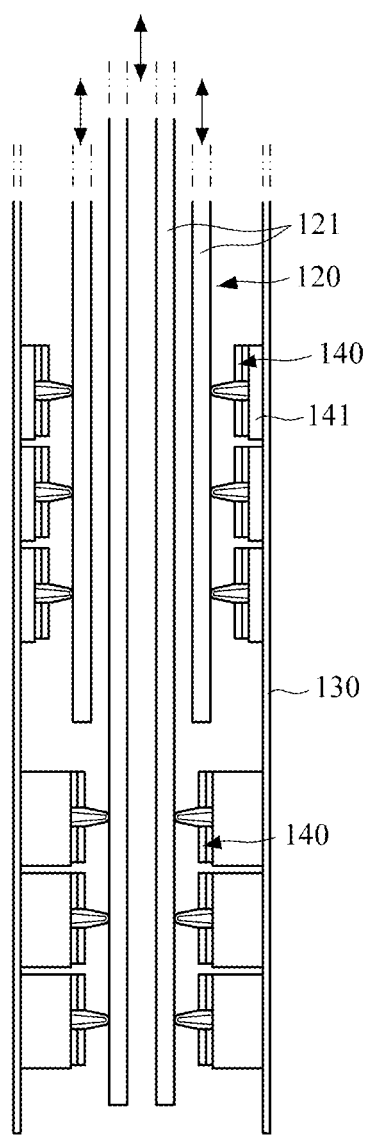
FIG. 2 is a diagram illustrating an internal structure of the surgical instrument of FIG. 1 according to an embodiment.

FIG. 1 illustrates a perspective view of a surgical instrument according to an embodiment. FIG. 2 illustrates an internal structure of the surgical instrument of FIG. 1, according to an embodiment.

Referring to FIGS. 1 and 2, the surgical instrument may be employed by a surgical robot to carry out minimally invasive surgery, and may include an end effecter 110, the power transmitting unit 120, a housing 130, and the piezoelectric driver 140.

The end effecter 110 may conduct a surgery in direct contact with a surgical area. The power transmitting unit 120 may transmit motive power of the piezoelectric drivers 140 to the end effecter 110 to drive the end effecter 110. The housing 130 may be designed to enclose the power transmitting unit 120. The piezoelectric driver 140 may generate motive power by use of an inverse piezoelectric effect of a piezoelectric element by which a stress is generated in response to application of an electric potential difference. The piezoelectric driver 140 may be designed to be compact. Hence, the piezoelectric driver 140 may be received in the housing 130 and provide motive power to the power transmitting unit 120.

As described above, the piezoelectric driver 140 is configured to be installed inside of a surgical instrument, that is, the housing 130, and thereby reducing a size of a surgical robot, compared to a configuration in which a driver such as an electric power driver that drives a wire is installed outside of a surgical instrument. In addition, since the surgical instrument drives the end effecter 110 by use of the piezoelectric driver 140, the surgical instrument may be usable in a magnetic resonance environment.

Figure 3:
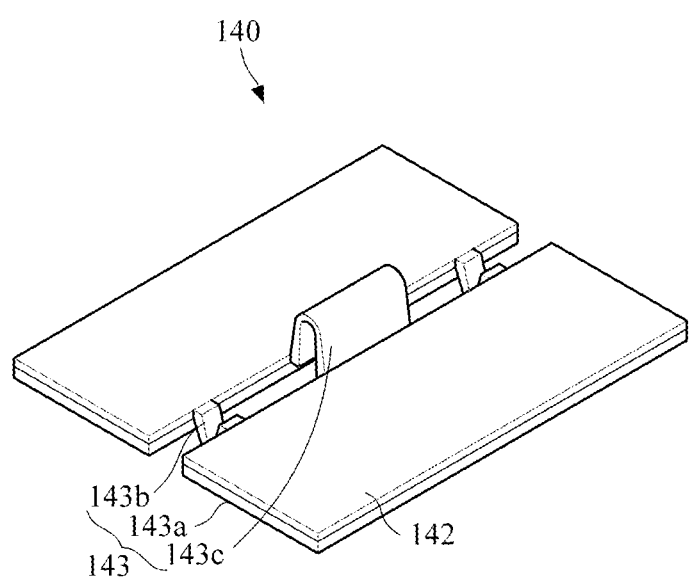
FIG. 3 is a diagram illustrating a perspective view of a piezoelectric driver according to an embodiment.

The power transmitting unit 120 may include at least one slider 121 that transmits the motive power to the end effecter 110 as the slider 121 moves linearly. Each of the sliders 121 may be formed of a rigid body. Thus, the power transmitting unit 120 does not have backlash, and is thus capable of accurate control compared a power transmitting unit using wires. Additionally, the power transmitting unit 120 may increase in life span without being stretched even when in long term use. In this example, the piezoelectric driver 140 is mounted in the housing 130 in a manner that surrounds the sliders 121, and moves the sliders 121 linearly. For example, as shown in FIG. 3, the piezoelectric drivers 140 may include a supporter 141, a pair of piezoelectric elements 142, and an elastic unit 143.

The supporter 141 may be fixed to an inner wall of the housing 130. The pair of piezoelectric elements 142 may be disposed to be spaced apart from each other on the supporter 141. The piezoelectric elements 142 may be made of piezoelectric ceramic. The elastic unit 143 may include a pair of elastic bodies 143a, fastening projections 143b, and a coupling tip 143c.

The pair of elastic bodies 143a may be fixed to the respective piezoelectric elements 142, and spaced apart from each other. The fastening projections 143b may fasten the elastic bodies 143a and the piezoelectric elements 142 to the supporter 141. Each of the fastening projections 143b may have one end connected to the elastic bodies 143a and another end fixed to the supporter 141. The coupling tip 143c may connect the elastic bodies 143a and be formed to be in contact with the slider 121.

Operation of each of the piezoelectric drivers 140 may be as follows. In response to a voltage which is applied to the piezoelectric elements 142 such that an opposite displacement is generated between the piezoelectric elements 142, spiral oscillation is generated on the coupling tip 143c. In this case, the oscillating direction of the coupling tip 143c may be set to a normal or reverse direction according to a voltage direction in which the voltage is applied to the piezoelectric elements 142. According to the oscillation direction of the coupling tip 143c, force is applied to the slider 121 to cause the slider 121 to move forward or backward. A plurality of piezoelectric drivers 140 may be disposed around the sliders 121 to increase the driving power applied to the sliders 121.

The power transmitting unit 120 may include a plurality of sliders 121 to transmit motive power independently to the end effecter 110. The sliders 121 may be disposed to operate in parallel to separately transmit the power to the end effecter 110. In this case, the piezoelectric drivers 140 may be mounted in the housing 130 to be disposed around the respective sliders 121 to linearly drive the sliders 121 independently from one another. Each of the piezoelectric drivers 140 may be configured as described above.

Figure 4:
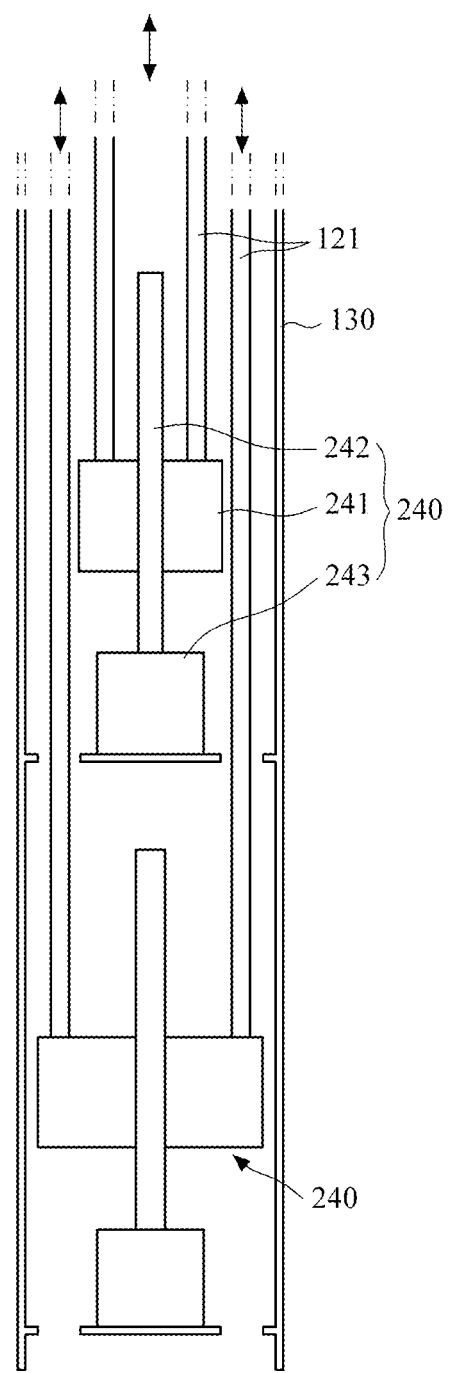
FIG. 4 is a diagram illustrating a piezoelectric driver according to another embodiment.
Figure 5:
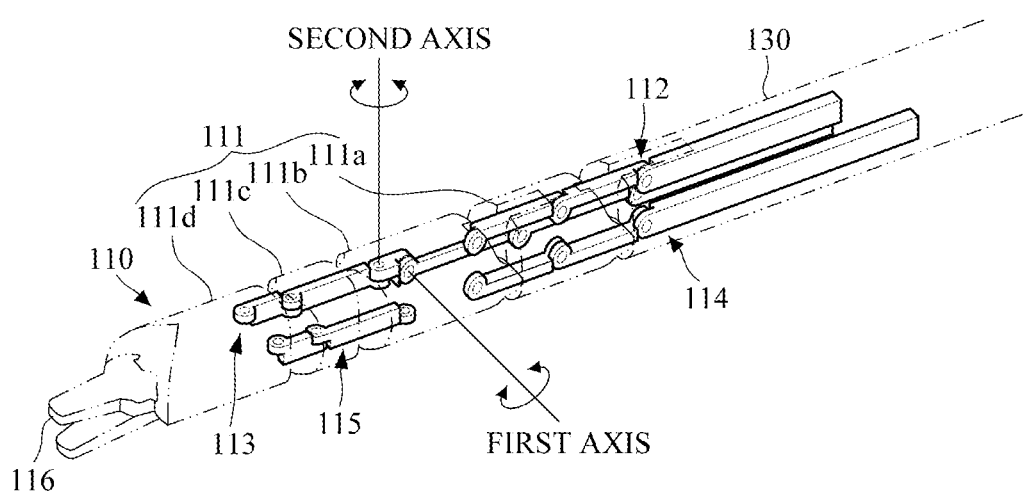
FIG. 5 is a diagram illustrating a perspective view of an inside of the surgical instrument having a two-degree-of-freedom rotation mechanism, which is shown in the example illustrated in FIG. 1, according to an embodiment.
Figure 6A:
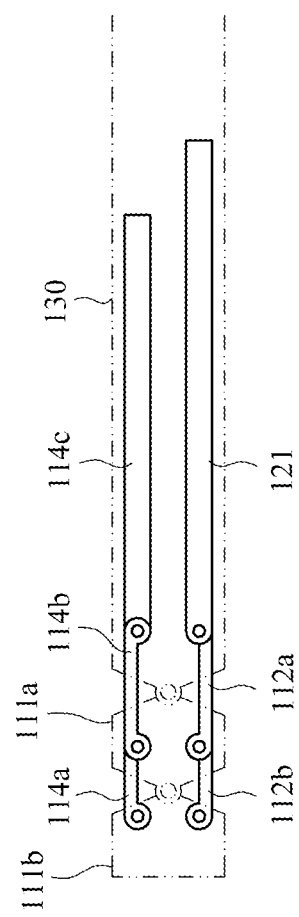
FIGS. 6A and 6B are diagrams illustrating a cross-sectional view for explaining how an end effecter shown in the embodiment illustrated in FIG. 5 is bent in a first axial direction.
Figure 6B:
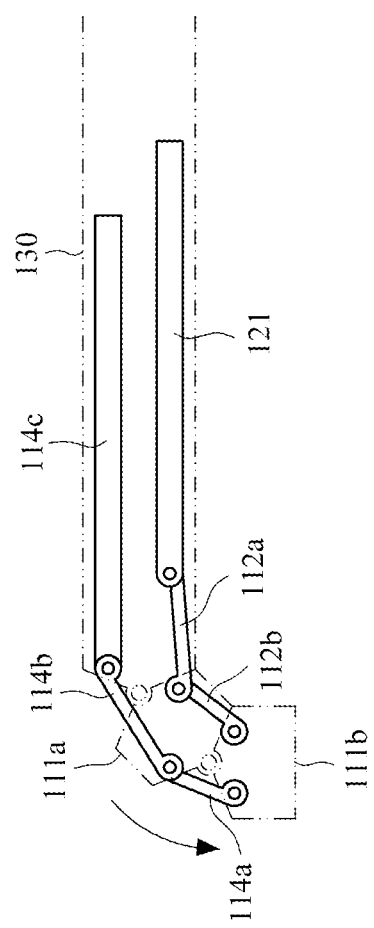

According to another embodiment, as shown in FIG. 4, a piezoelectric driver 240 may include an inertial resistance member 241, a friction shaft 242, and a piezoelectric element 243. The inertial resistance member 241 may be fixed to one end of the slider 121. The friction shaft 242 may penetrate the inertial resistance member 241 to cause friction against the inertial resistance member 241. The piezoelectric element 243 may be mounted in the housing 130, and extend and compress along a moving direction of the slider 121 to thereby linearly move the friction shaft 242.

The above piezoelectric driver 240 may operate as follows. If the piezoelectric element 243 oscillates by repeatedly extending and restoring, the inertial resistance member 241 may move forward according to inertia. Accordingly, the slider 121 may be driven to move forward along with the inertial resistance member 241. In contrast, when the piezoelectric element 243 oscillates by repeatedly compressing and restoring, the inertial resistance member 241 may move backward according to inertia. Thus, the slider 121 may be driven to move backward along with the inertial resistance member 241.

In this case, when a plurality of sliders 121 are provided to provide motive power independently to the end effecter 110, a plurality of piezoelectric drivers 240 may be provided in the housing 130, and disposed to correspond to the respective sliders 121 to linearly move the corresponding sliders 121 independently from one another.

The end effecter 110 with a two-degree of bending freedom mechanism may be configured as follows. Referring to examples illustrated in FIGS. 5 to 7B, an end effecter 110 may include a frame unit 111, a first axis driving link unit 112, and a second axis driving link unit 113. The frame unit 111 may include a first frame 111a, a second frame 111b, a third frame 111c, and a fourth frame 111d. The first frame 111a may be joint-connected to the housing 130 to be rotatable in a first axial direction. The second frame 111b may be joint-connected to the first frame 111a to be rotatable in the first axial direction. The third frame 111c may be joint-connected to the second frame 111b to be rotatable in a second axial direction which is perpendicular to the first axial direction. The fourth frame 111d may be joint-connected to the third frame 111c to be rotatable in the second axial direction.

The first axis driving link unit 112 may include a first driving link 112a and a second driving link 112b. The first driving link 112a may have one end connected to one of sliders 121 to be rotatable in the first axial direction in the housing 130. The second driving link 112b may have one end connected to the other end of the first link 112a to be rotatable in the first axial direction in the first frame 111a, and the other end rotatably supported in the second frame 111b.

The second driving link unit 113 may include a third driving link 113a, a fourth driving link 113b, a fifth driving link 113c, a sixth driving link 113d, and a two-axis joint 113e. The third driving link 113a may have one end connected to one of the remaining sliders 121 which are not connected to the first driving link 112a to be rotatable in the first axial direction in the housing 130. The fourth driving link 113b may have one end connected to the other end of the third driving link 113a to be rotatable in the first axial direction in the first frame 111a.

The two-axis joint 113e may be connected to the other end of the fourth driving link 113b to be rotatable in the first axial direction in the second frame 111b. The fifth driving link 113c may have one end connected to the two-axis joint 113e to be rotatable in the second axial direction in the second frame 111b. The sixth driving link 113d may have one end connected to the other end of the fifth driving link 113c to be rotatable in the second axial direction in the third frame 111c, and the other end rotatably supported in the fourth frame 111d.

Aspects of the above end effecter 110 will be described below. Referring to the examples illustrated in FIGS. 6A and 6B, in response to motive power applied from one of the sliders 121, the first driving link 112a may rotate about the slider 121 in the first axial direction, and enable the first frame 111a to be bent in the first axial direction with respect to the housing 130. At this time, the second driving link 112b may rotate about the first driving link 112a in the first axial direction, and enable the second frame 111b to be bent in the first axial direction with respect to the first frame 111a.

Figure 7A:
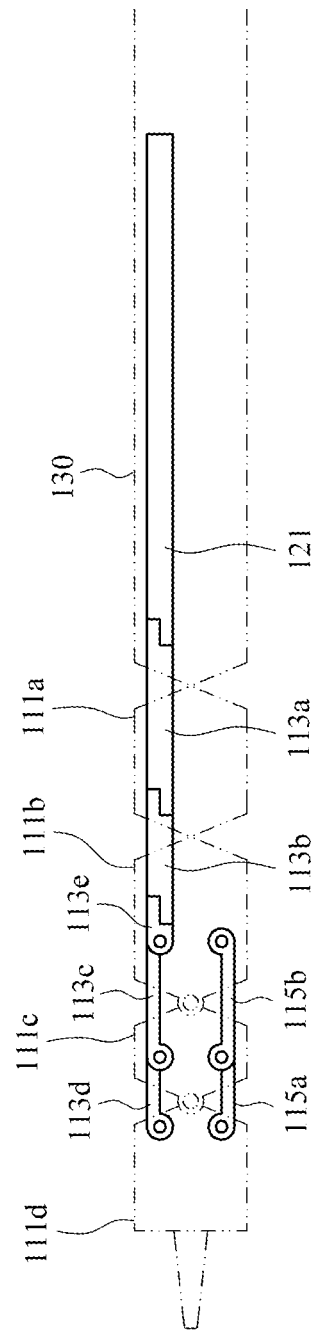
FIGS. 7A and 7B are diagrams illustrating a cross-sectional view for explaining how the end effecter shown in the embodiment illustrated in FIG. 5 is bent in a second axial direction.
Figure 7B:
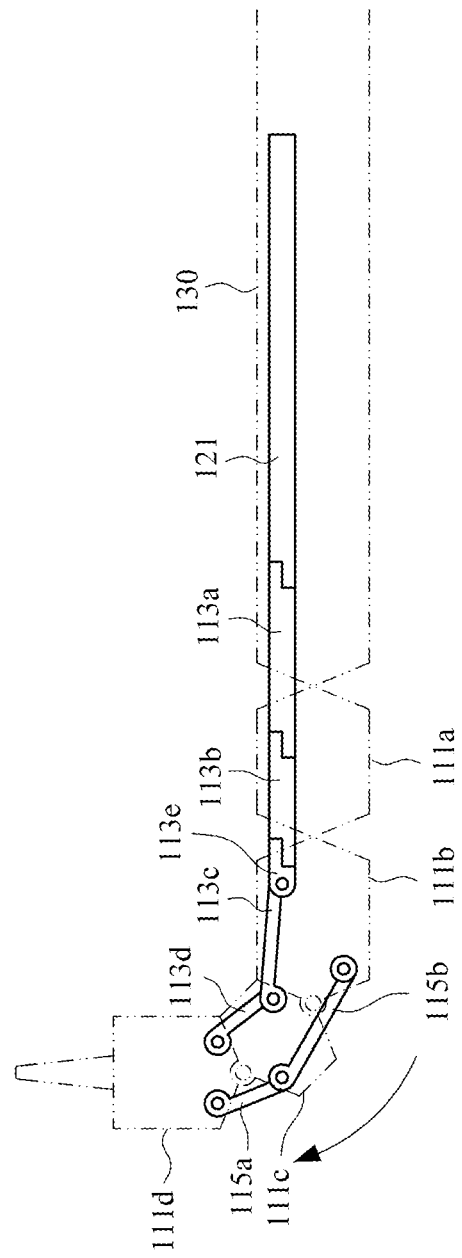

In addition, referring to the examples illustrated in FIGS. 7A and 7B, in response to motive power applied from one of the remaining sliders 121, the third driving link 113a may rotate about the slider 121 in the first axial direction, and thereby may not restrict bending of the first frame 111a. The fourth driving link 113b may rotate about the third driving link 113a in the first axial direction, and thereby may not restrict bending of the second frame 111b.

A first axial directional rotation force of the fourth driving link 113b may be converted into a second axial directional rotation force via the two-axis joint 113e, and be transmitted to the fifth driving link 113c. Then, the fifth driving link 113c may rotate about the two-axis joint 113e in the second axial direction, enabling the third frame 111c to be bent in the second axial direction. The sixth driving link 113d may rotate about the fifth driving link 113c in the second axial direction, enabling the fourth frame 111d to be bent with respect to the third frame 111c in the second axial direction. Therefore, an end of the fourth frame 111d has a two-degree of bending freedom mechanism.

The end effecter 110 may include a first axis restriction link unit 114, and a second axis restriction link unit 115. The first axis restriction link unit 114 may restrict the first and second frames 111a and 111b to be stably bent in the first axial direction by the first axis driving link unit 112. The first axis restriction link unit 114 may include a first restriction link 114a, a second restriction link 114b, and a third restriction link 114c. The first restriction link 114a may have an end supported in the second frame 111b in a manner that is rotatable in the first axial direction. The second restriction link 114b may be connected to the other end of the first restriction link 114a in the first frame 111a in a manner that is rotatable in the first axial direction. The third restriction link 114c may have an end connected to the other end of the second restriction link 114b in a manner that is rotatable in the first axial direction, and have the other end supported in a manner that is movable in the housing 130.

The second restriction link unit 115 may restrict the third and fourth frames 111c and 111d to be stably bent in the second axial direction by the second axis driving link 113. The second restriction link unit 115 may include a fourth restriction link 115a and a fifth restriction link 115b. The fourth restriction link 115a may have an end supported in the fourth frame 111d in a manner that is rotatable in the second axial direction. The fifth restriction link 115b may have an end connected to the other end of the fourth restriction link 115a in the third frame 111c in a manner that is rotatable in the second axial direction, and have the other end supported in a manner that is movable in the second frame 111b.

The end effecter 110 may have a one-degree-of-freedom grip mechanism. For example, the end effecter 110 may include a forceps 116. The forceps 116 may be mounted to a terminal end of the fourth frame 111d. The forceps 116 may be rotated enough to be opened and closed under the control of a forceps manipulating unit (not illustrated). The forceps manipulating unit may rotate at least one of both jaws of the forceps 116 in the fourth frame 111d using the motive power provided from the piezoelectric driver 140 or 240 which is described above. The forceps manipulating unit may include a slider to be moved linearly by the piezoelectric driver 140 or 240, and a link unit to rotate at least one of the jaws of the forceps 116 by converting the linear movement of the slider into rotary movement.

Figure 8:
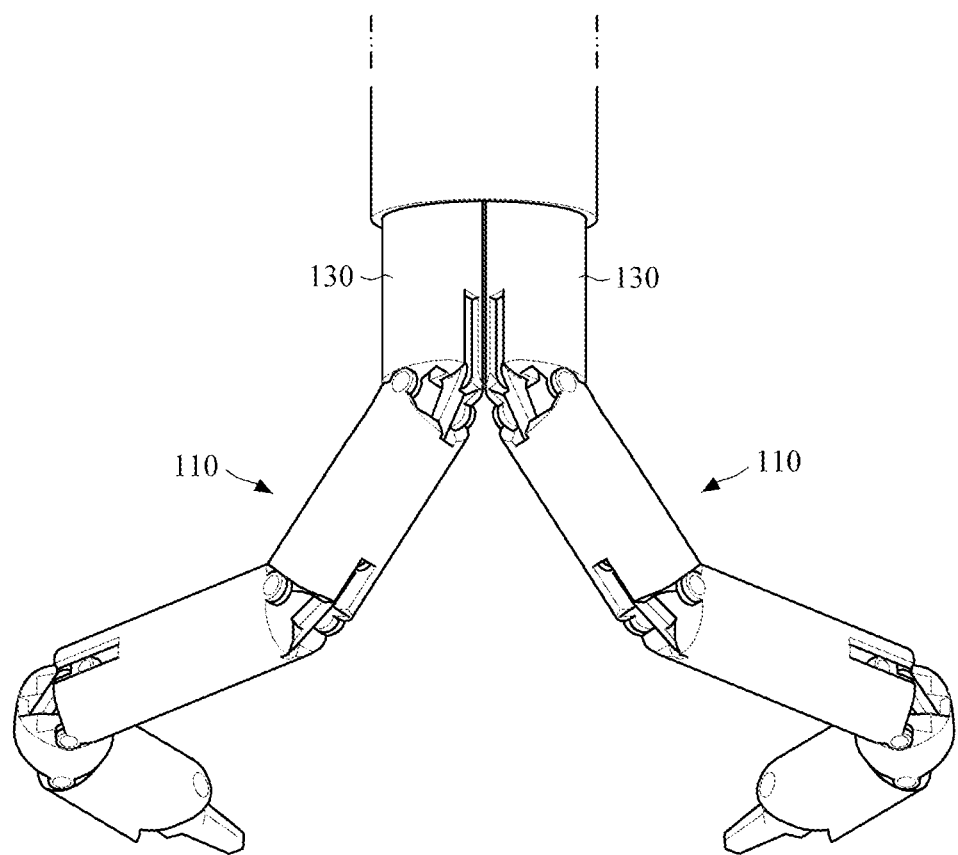
FIG. 8 is a diagram illustrating a perspective view of a surgical instrument having a plurality of end effecters according to an embodiment.

As shown in FIG. 8, a plurality of end effecters 110 may be provided. The end effecters 110 may be allowed to move independently from one another by the above-described piezoelectric drivers 140 or 240 and the power transmitting unit 120. In this case, the end effecters 110 may be connected to the housings 130 one by one. Each of the housings 130 may receive the piezoelectric driver 140 or 240 and the power transmitting unit 120 to move the end effecter 110 connected to the housing 130. As described above, in a case in which the surgical instrument consists of multiple joints, independent control of movement over each of the joints may be possible. Even with the increase of the number of joints, joints are not affected by one another, and thus the surgical instrument may be easy to be developed to a multiple joint configuration.

Figure 9:
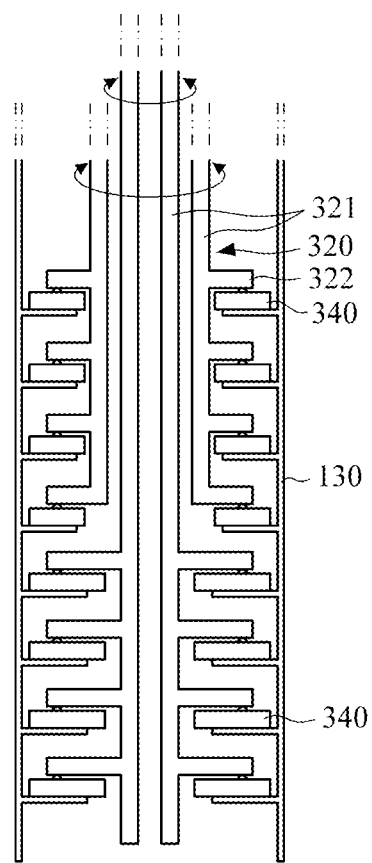
FIG. 9 is a diagram illustrating a power transmitting unit and a piezoelectric driver according to another embodiment.

According to another embodiment, referring to FIG. 9, a power transmitting unit 320 may include a rotor 321 to transfer the motive power to the end effecter 110 through rotating movement. In this case, a piezoelectric driver 340 may be mounted in the housing 130 to rotate the rotor 321.

Figure 10:
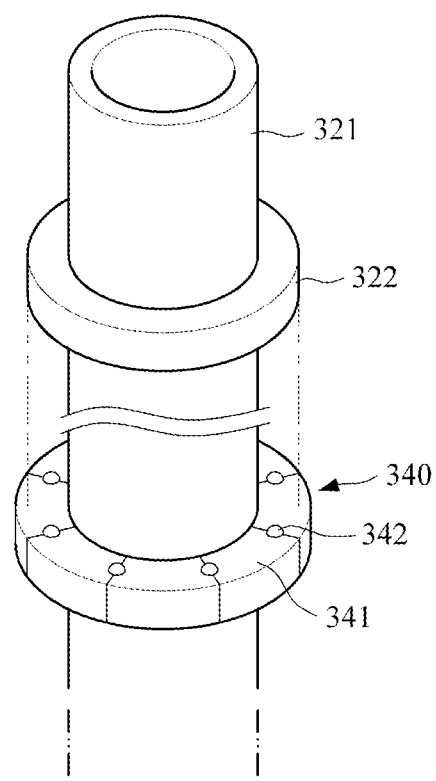
FIG. 10 is a diagram illustrating a perspective view of the piezoelectric driver shown in FIG. 9 according to an embodiment.

As one example, as shown in the example illustrated in FIG. 10, the piezoelectric driver 340 may have a plurality of piezoelectric elements 341 supported and arranged in a circular form that corresponds to a form of one end of the rotor 321, and pushers 342 formed on surfaces of the piezoelectric elements 341 facing toward the end of the rotor 321. When a voltage is applied, which causes an opposite displacement between neighboring piezoelectric elements 341, oscillation is generated on the pushers 342. In this example, the oscillating direction of the pushers 342 may be set to rotate the rotor 321 in a normal direction or in a reverse direction according to a voltage direction in which the voltage is applied to the piezoelectric elements 341. Thus, by controlling the direction of voltage applied to the piezoelectric elements 341, it is allowed to rotate the rotor 321 in a normal direction or in a reverse direction.

The rotor 321 may include a plurality of blades 322 which are arranged around a circumference of the rotor 321 and spaced apart from one another along an axial direction. In this case, a plurality of piezoelectric drivers 340 may be mounted in the housing 130 to correspond to the respective blades 322. Hence, motive power provided to the rotor 321 is increased, thereby allowing the rotor 321 to rotate more smoothly.

In this example, the power transmitting unit 320 may include a plurality of rotors 321 to provide independent motive power to an end effecter. The rotors 321 may rotate in parallel to individually provide motive power to the end effecter. In this case, a plurality of piezoelectric drivers 340 may be mounted in the housing 130 to be arranged, respectively, around the circumferences of the rotors 321 and to independently rotate the rotors 321. Each of the rotors 321 may include a hollow and the rotors 321 may be arranged coaxially in the housing 130.

The rotors 321 and the piezoelectric drivers 340 as shown in the examples illustrated in FIGS. 9 and 10 may enable the end effecter to have a two-degree-of-freedom rotation mechanism. For example, the end effecter may include a frame and a forceps. The frame may be connected to the housing 130 in a manner that is rotatable in the same direction as the rotation direction of the rotors 321. Further, the frame may be rotatably connected to one of the rotors 321. The forceps may be connected to a terminal end of the frame in a manner that is rotatable in the same direction as the rotation direction of the rotors 321. The forceps may be rotatably connected to of the other rotor 321. The forceps may be configured to have a one-degree-of-freedom grip mechanism.

A number of exemplary embodiments have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A surgical instrument comprising:
   at least one end effecter configured to conduct a surgical operation;
   at least one piezoelectric driver configured to generate motive power;
   a power transmitting unit configured to transmit the motive power generated by the at least one piezoelectric driver to the at least one end effecter to operate the at least one end effecter; and
   a housing which encloses the power transmitting unit and the at least one piezoelectric driver
   wherein the at least one piezoelectric driver comprises a pair of piezoelectric elements that are spaced apart from each other, a pair of elastic bodies fixed to the respective piezoelectric elements and spaced apart from each other, and a coupling tip which connects the elastic bodies and is in contact with the power transmitting unit.

2. The surgical instrument of claim 1, wherein the power transmitting unit comprises a slider configured to move linearly to transmit the motive power to the at least one end effecter, and the at least one piezoelectric driver is disposed around a circumference of the slider and linearly moves the slider.

3. The surgical instrument of claim 2, wherein the at least one piezoelectric driver further comprises:
   a supporter that is fixed to an inner wall of the housing; and
   fastening projections that fasten the pair of elastic bodies to the supporter, and
   wherein the coupling tip is in contact with the slider.

4. A surgical instrument comprising:
   at least one end effecter configured to conduct a surgical operation;
   at least one piezoelectric driver configured to generate motive power;
   a power transmitting unit configured to transmit the motive power generated by the at least one piezoelectric driver to the at least one end effecter to operate the at least one end effecter; and
   a housing which encloses the power transmitting unit and the at least one piezoelectric driver,
   wherein the power transmitting unit comprises a plurality of sliders, each of the sliders configured to move linearly to transmit motive power to the at least one end effecter, and the at least one piezoelectric driver comprises a plurality of piezoelectric drivers that are disposed around the sliders and linearly move the sliders independently from one another, and
   wherein the at least one end effecter comprises:
   a frame unit comprising a first frame that is joint-connected to the housing and is rotatable in a first axial direction, a second frame that is joint-connected to the first frame and is rotatable in the first axial direction, a third frame that is joint-connected to the second frame and is rotatable in a second axial direction that is perpendicular to the first axial direction, and a fourth frame that is joint-connected to the third frame and is rotatable in the second axial direction,
   a first axis driving link unit comprising a first driving link having a first end that is connected to one of the sliders and is rotatable in the first axial direction, and a second driving link having a first end that is connected to a second end of the first driving link in the first frame and is rotatable in the first axial direction and a second end that is supported rotatably in the second frame, and
   a second axis driving link unit comprising a third driving link having a first end that is connected to another one of the sliders and is rotatable in the first axial direction, a fourth driving link having a first end that is connected to a second end of the third driving link in the first frame and is rotatable in the first axial direction, a two-axis joint that is connected to a second end of the fourth driving link in the second frame and is rotatable in the first axial direction, a fifth driving link having a first end that is connected to the two-axis joint in the second frame and is rotatable in the second axial direction, and a sixth driving link having a first end that is connected to a second end of the fifth driving link in the third frame and is rotatable in the second axial direction and a second end that is supported rotatably in the fourth frame.

5. The surgical instrument of claim 4, wherein the at least one end effecter comprises:
   a first axis restriction link unit comprising a first restriction link having a first end that is supported in the second frame and is rotatable in the first axial direction, a second restriction link having a first end that is connected to a second end of the first restriction link in the first frame and is rotatable in the first axial direction, and a third restriction link having a first end that is connected to a second end of the second restriction link in the housing and is rotatable in the first axial direction and a second end that is supported movably in the housing, and
   a second axis restriction link unit comprising a fourth restriction link having a first end that is supported in the fourth frame and is rotatable in the second axial direction, and a fifth restriction link having a first end that is connected to a second end of the fourth restriction link in the third frame and is rotatable in the second axial direction and a second end that is supported movably in the second frame.

6. The surgical instrument of claim 5, wherein the at least one end effecter comprises a plurality of end effecters, and each of end effecters is movable independently from the other end effectors by the piezoelectric driver and the power transmitting unit.

7. The surgical instrument of claim 1, wherein the power transmitting unit comprises a slider to transmit motive power to the at least one end effecter, and the at least one piezoelectric driver comprises an inertial resistance member that is fixed to one end of the slider, a friction shaft that penetrates the inertial resistance member to generate friction against the inertial resistance member, and a piezoelectric element that is mounted in the housing and extends and compresses along a moving direction of the slider to thereby linearly move the friction shaft.

8. The surgical instrument of claim 7, wherein the power transmitting unit comprises a plurality of sliders configured to move linearly to transmit motive power to the at least one end effecter, and the at least one piezoelectric driver comprises a plurality of piezoelectric drivers that are mounted in the housing to correspond to the respective sliders to linearly move the sliders independently from the one another.

9. The surgical instrument of claim 8, wherein the at least one end effecter comprises:
- a frame unit comprising a first frame that is joint-connected to the housing and is rotatable in a first axial direction, a second frame that is joint-connected to the first frame and is rotatable in the first axial direction, a third frame that is joint-connected to the second frame and is rotatable in a second axial direction that is perpendicular to the first axial direction, and a fourth frame that is joint-connected to the third frame and is rotatable in the second axial direction,
- a first axis driving link unit comprising a first driving link having a first end that is connected to one of the sliders and is rotatable in the first axial direction and a second driving link having a first end that is connected to a second end of the first driving link in the first frame and is rotatable in the first axial direction and a second end that is supported rotatably in the second frame, and
- a second axis driving link unit comprising a third driving link having a first end that is connected to one of the remaining sliders and is rotatable in the first axial direction in the housing, a fourth driving link having a first end that is connected to a second end of the third driving link in the first frame and is rotatable in the first axial direction, a two-axis joint that is connected to a second end of the fourth driving link in the second frame and is rotatable in the first axial direction, a fifth driving link having a first end that is connected to the two-axis joint in the second frame and is rotatable in the second axial direction, and a sixth driving link having a first end that is connected to a second end of the fifth driving link in the third frame and is rotatable in the second axial direction and a second end that is supported rotatably in the fourth frame.

10. The surgical instrument of claim 9, wherein the at least one end effecter further comprises:
- a first axis restriction link unit comprising a first restriction link having a first end that is supported in the second frame and is rotatable in the first axial direction, a second restriction link having a first end that is connected to a second end of the first restriction link in the first frame and is rotatable in the first axial direction, and a third restriction link having a first end that is connected to a second end of the second restriction link in the housing and is rotatable in the first axial direction and a second end that is supported movably in the housing, and
- a second axis restriction link unit comprising a fourth restriction link having a first end that is supported in the fourth frame and is rotatable in the second axial direction and a fifth restriction link having a first end that is connected to a second end of the fourth restriction link in the third frame and is rotatable in the second axial direction and a second end that is supported movably in the second frame.

11. The surgical instrument of claim 10, wherein the at least on end effecter comprises a plurality of end effecters that are movable independently from one another by the at least one piezoelectric driver and the power transmitting unit.

12. The surgical instrument of claim 1, wherein the power transmitting unit comprises a rotor to transmit the motive power to the end effecter through rotational movement, and the at least one piezoelectric driver is mounted in the housing to rotate the rotor.

13. The surgical instrument of claim 12, wherein the at least one piezoelectric driver comprises a plurality of piezoelectric elements that are supported and arranged in a circular form that corresponds to a form of one end of the rotor in the housing, and pushers formed on surfaces of the piezoelectric elements facing toward the end of the rotor.

14. The surgical instrument of claim 13, wherein the rotor comprises a plurality of blades which are arranged around a circumference of the rotor and spaced apart from one another along an axial direction of the rotor, and the plurality of piezoelectric drivers are mounted in the housing to correspond to the respective blades.

15. The surgical instrument of claim 13, wherein the power transmitting unit comprises a plurality of rotors configured to rotate in parallel to individually transmit the motive power to the at least one end effecter, and the plurality of piezoelectric drivers are disposed around a circumference of the rotors and rotate the rotors independently from one another.

* * * * *